(12) United States Patent
Sawanoi et al.

(10) Patent No.: US 11,382,523 B2
(45) Date of Patent: Jul. 12, 2022

(54) INSTRUMENT HAVING A BLOOD PRESSURE MEASURING FUNCTION

(71) Applicant: OMRON HEALTHCARE CO., LTD., Muko (JP)

(72) Inventors: Yukiya Sawanoi, Kyoto (JP); Yoshihiko Sano, Kyoto (JP); Brian Brigham, Kyoto (JP); Takeshi Kubo, Kyoto (JP)

(73) Assignee: OMRON HEALTHCARE CO., LTD., Kyoto (JP)

( * ) Notice: Subject to any disclaimer, the term of this patent is extended or adjusted under 35 U.S.C. 154(b) by 241 days.

(21) Appl. No.: 16/026,173

(22) Filed: Jul. 3, 2018

(65) Prior Publication Data
US 2018/0310835 A1 Nov. 1, 2018

Related U.S. Application Data

(63) Continuation of application No. PCT/JP2016/088957, filed on Dec. 27, 2016.

(30) Foreign Application Priority Data

Jan. 4, 2016 (JP) .............................. JP2016-000262

(51) Int. Cl.
*A61B 5/0225* (2006.01)
*A61B 5/021* (2006.01)
(Continued)

(52) U.S. Cl.
CPC ........ *A61B 5/0225* (2013.01); *A61B 5/02141* (2013.01); *A61B 5/02233* (2013.01);
(Continued)

(58) Field of Classification Search
CPC ... A61B 5/0225; A61B 5/021; A61B 5/02141; A61B 5/02233; A61B 5/681;
(Continued)

(56) References Cited

U.S. PATENT DOCUMENTS

2006/0058687 A1* 3/2006 Kishimoto ......... A61B 5/02233
600/499
2008/0071180 A1* 3/2008 Borgos ................. A61B 5/7239
600/500
(Continued)

FOREIGN PATENT DOCUMENTS

JP H09-038052 A 2/1997
JP 2004-254717 A 9/2004
(Continued)

OTHER PUBLICATIONS

Jan. 28, 2020 Office Action issued in Japanese Patent Application No. 2016-000262.
(Continued)

*Primary Examiner* — Charles A Marmor, II
*Assistant Examiner* — Deirdre M Willgohs
(74) *Attorney, Agent, or Firm* — Oliff PLC

(57) ABSTRACT

The instrument according to the present invention includes a band-like belt worn around a wrist, and a main body disposed at a portion of the belt corresponding to the volar surface or the dorsal surface of the wrist. An element for executing a blood pressure measuring function is mounted in the main body. A battery for supplying electric power to the element mounted in the main body is disposed at a portion of the belt located away from the main body in the circumferential direction around the wrist. A wire is provided in the belt, extends in the circumferential direction along the fluid bag, and electrically connects the element mounted in the main body and the battery. In the belt, the wire is disposed away from the fluid bag in the width direction perpendicular to the circumferential direction and extends along an edge section of the belt.

6 Claims, 8 Drawing Sheets

(51) Int. Cl.
*A61B 5/022* (2006.01)
*A61B 5/00* (2006.01)
*A61B 5/107* (2006.01)

(52) U.S. Cl.
CPC .............. *A61B 5/107* (2013.01); *A61B 5/681* (2013.01); *A61B 5/6824* (2013.01)

(58) Field of Classification Search
CPC ..... A61B 5/6824; A61B 17/132; A61B 17/12; A61B 17/135; A61F 5/30
USPC ................................................. 600/485–499
See application file for complete search history.

(56) References Cited

U.S. PATENT DOCUMENTS

2009/0124913 A1* 5/2009 Yamashita ........... A61B 5/0225
600/499

2014/0350419 A1* 11/2014 Doi .................... A61B 5/02233
600/499

FOREIGN PATENT DOCUMENTS

| | | |
|---|---|---|
| JP | 2006-81655 A | 3/2006 |
| JP | 2008-161687 A | 7/2008 |
| JP | 4414485 B1 | 2/2010 |
| JP | 2010-069196 A | 4/2010 |
| JP | 2013-143997 A | 7/2013 |
| KR | 2015-0092465 A | 8/2015 |

OTHER PUBLICATIONS

Mar. 25, 2019 Extended Search Report issued in European Patent Application No. 16883869.6.

Mar. 7, 2017 International Search Report issued in International Patent Application No. PCT/JP2016/088957.

* cited by examiner

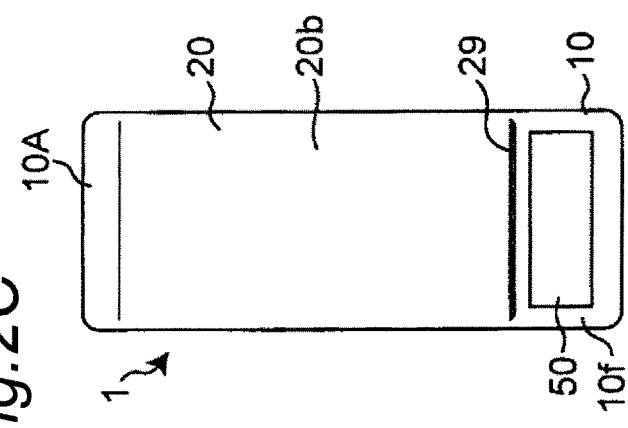
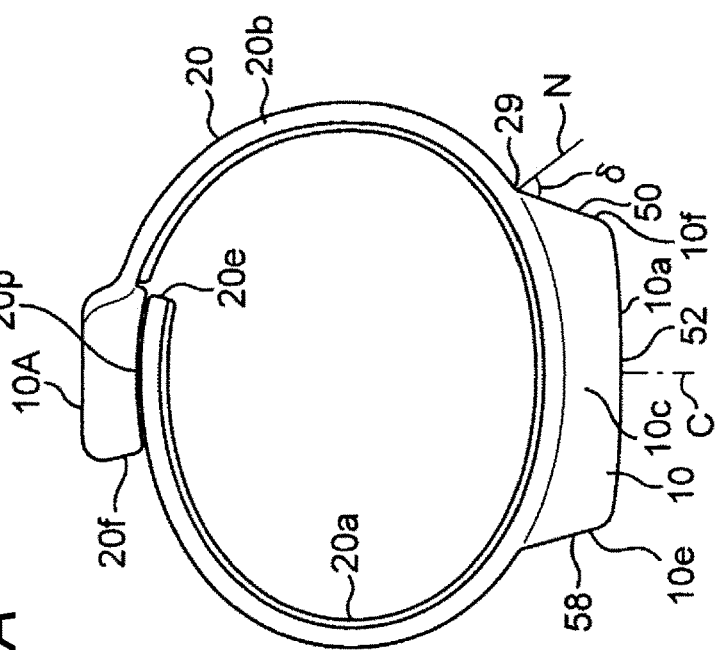
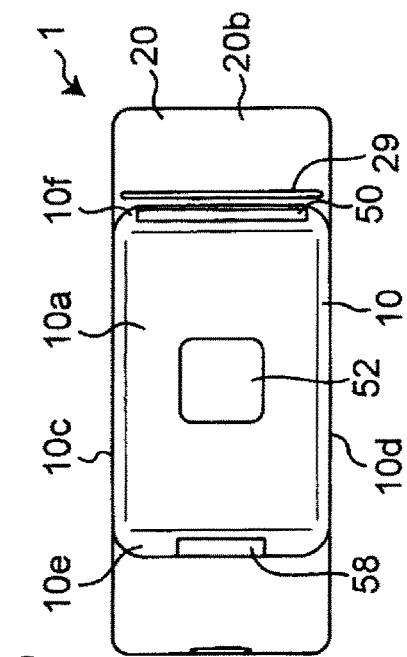
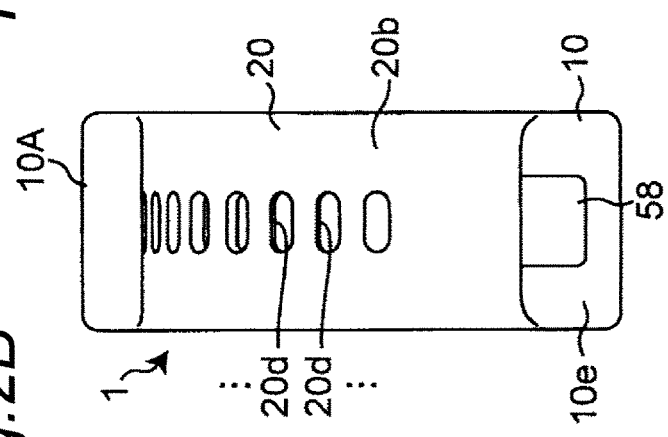

INSTRUMENT HAVING A BLOOD PRESSURE MEASURING FUNCTION

CROSS-REFERENCE TO RELATED APPLICATIONS

This is a continuation application of International Application No. PCT/JP2016/088957, with an International filing date of Dec. 27, 2016, which claims priority of Japanese Patent Application No. 2016-000262 filed on Jan. 4, 2016, the entire content of which is hereby incorporated by reference.

TECHNICAL FIELD

The present invention relates to an instrument and, more particularly, to an instrument having a blood pressure measuring function and worn around a wrist.

BACKGROUND ART

Conventionally, as an example of the above type of instrument, an instrument disclosed in Patent Literature 1 (JP 09-38052 A) is known. The instrument includes a cuff band worn around a wrist, and a blood pressure monitor main body disposed at a portion of the cuff band intended to correspond to the volar surface (surface corresponding to the palm side) of the wrist. The blood pressure monitor main body contains a battery that supplies electric power to elements (a pump, a control circuit, and the like) for measuring blood pressure disposed in the main body.

SUMMARY OF INVENTION

However, in the above instrument, outer dimensions of the main body such as the thickness in the direction perpendicular to the outer circumferential surface of the wrist are relatively large. As a result, there is a problem that when a user wears and uses the instrument at all times, the instrument becomes a hindrance in user's daily activities.

Therefore, an object of the present invention is to provide an instrument which has a blood pressure measuring function, is worn around a wrist, and includes a main body that may have reduced outer dimensions.

As a result of analyzing the instrument of the above conventional example, the inventors of the present disclosure have focused on the fact that the volume of the battery is the largest in the blood pressure monitor main body. If the battery is disposed separately from the blood pressure monitor main body, the outer dimensions of the main body, such as the thickness in the direction perpendicular to the outer circumferential surface of the wrist, can be reduced. However, there is a possibility that noise may occur in a wire that electrically connects the main body and the battery. Therefore, it is considered that countermeasures for the noise will be necessary.

In order to solve the above-described problem, the present disclosure provides an instrument having a blood pressure measuring function and worn around a wrist, the instrument comprising:

a band-like belt which is worn around a wrist in a circumferential direction, the band-like belt including a fluid bag that extends in the circumferential direction to compress an artery of the wrist; and a main body which is disposed at a portion of the band-like belt corresponding to one of a volar surface and a dorsal surface of the wrist, in which at least a pressure control unit that supplies air to the fluid bag and controls pressure is mounted as an element for executing the blood pressure measuring function, wherein a battery which supplies electric power to the element mounted in the main body is disposed at a portion of the band-like belt away from the main body in the circumferential direction, wherein a wire which extends in the circumferential direction along the fluid bag and electrically connects the battery and the element mounted in the main body is provided in the band-like belt, and wherein, in the band-like belt, the wire is disposed away from the fluid bag in a width direction perpendicular to the circumferential direction and is disposed along an edge section of the band-like belt.

The "volar surface" of the wrist, as used herein, means a portion of the outer circumferential surface of the wrist corresponding to the palm side. The "dorsal surface" of the wrist means a portion of the outer circumferential surface of the wrist corresponding to the back-of-hand side.

In addition, the "wrist" may be either a left wrist or a right wrist.

BRIEF DESCRIPTION OF DRAWINGS

The present invention will become more fully understood from the detailed description given hereinbelow and the accompanying drawings which are given by way of illustration only, and thus are not limitative of the present invention, and wherein:

FIG. 2A is a view illustrating the instrument as viewed in the direction of arrow A in FIG. 1 in a state where a main body of the instrument is located on the lower side. FIGS. 2B, 2C, and 2D are views illustrating the instrument as viewed from the left side, the right side, and the lower side in FIG. 2A, respectively.

DESCRIPTION OF EMBODIMENT

Hereinafter, an embodiment of the present invention will be described in detail with reference to the drawings.

Configuration of Instrument

Figure 1:
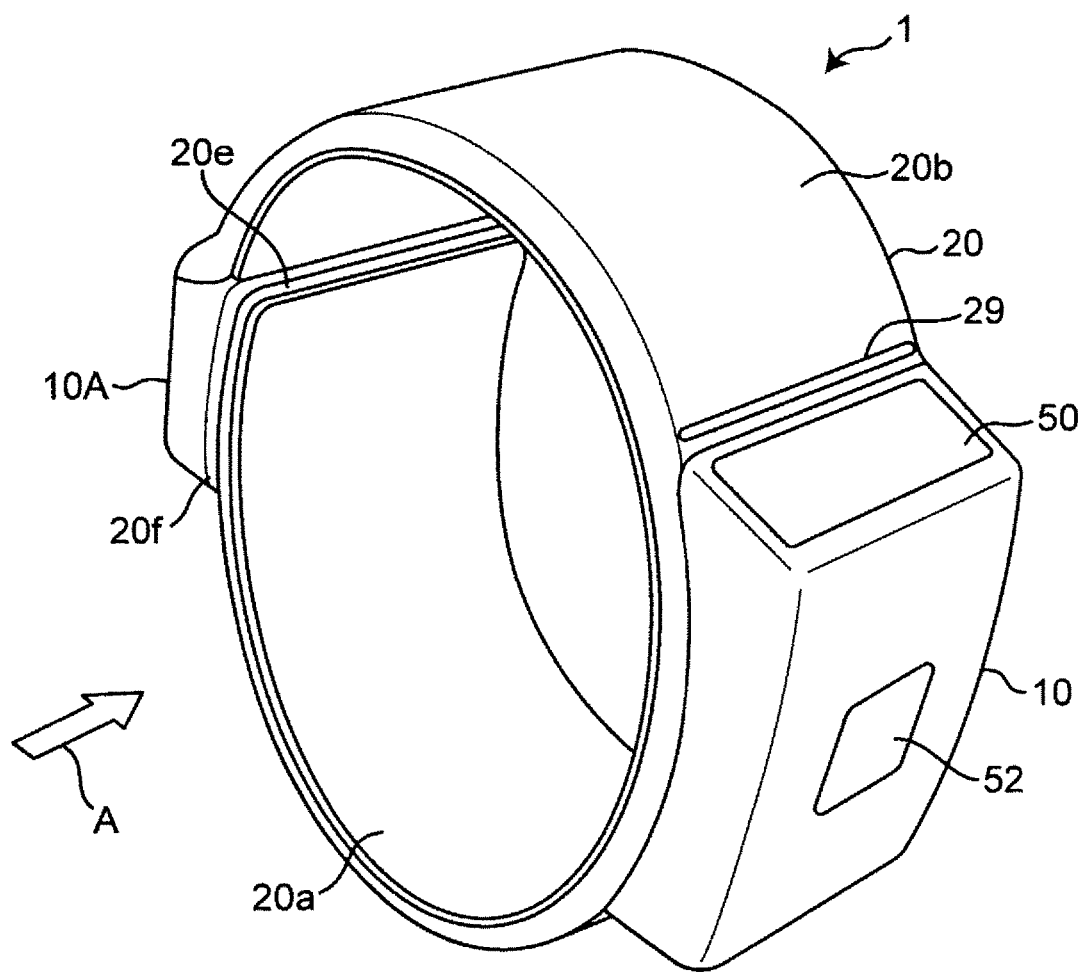
FIG. 1 is a perspective view illustrating an external appearance of an instrument according to an embodiment of the present invention.

FIG. 1 illustrates an outer appearance of an instrument (denoted by reference sign 1 as a whole) having a plurality of functions including a blood pressure measuring function, according to an embodiment of the present invention, when viewed obliquely. FIG. 2A illustrates the instrument 1 viewed in the direction of arrow A in FIG. 1 in a state where a main body 10 of the instrument 1 is located on the lower side. FIGS. 2B, 2C, and 2D illustrate the instrument 1 viewed from the left side, the right side, and the lower side in FIG. 2A, respectively. The instrument 1 is intended to be worn around a left wrist 90 of a user (see FIG. 5 to be described later).

As illustrated in these figures, the instrument 1 includes, as major components, a belt 20 to be wound around the left wrist 90 of the user, a main body 10 integrally attached to the belt 20, and a battery housing case 10A.

As FIGS. 1 and 2A clearly illustrate, the belt 20 has an elongated band-like shape so as to surround the left wrist 90 along the circumferential direction, and includes an inner layer 20a to be in contact with the left wrist 90 and an outer layer 20b facing the inner layer 20a. In this example, edges of the inner layer 20a and the outer layer 20b are welded together such that the inner layer 20a and the outer layer 20b form a bag shape. In the belt 20, a fluid bag 21 (see FIG. 3) for compressing the left wrist is contained.

In a state where the instrument 1 is worn around the left wrist 90 (hereinafter referred to as a "worn state"), one end section 20e and the other end section 20f of the belt 20 overlap in the circumferential direction such that the one end section 20e is located on the inner side and the other end section 20f is located on the outer side. In this example, the one end section 20e and the other end section 20f of the belt 20 overlap in a certain range in the circumferential direction (in this example, a range approximately matching the size of the battery housing case 10A). As a result of this overlap, in a case where blood pressure is measured by compressing the left wrist 90 with the belt 20, a substantially entire circumference of the left wrist 90 can be reliably compressed and accuracy of blood pressure measurement can be improved.

In this example, as illustrated in FIG. 2B, in order to keep the belt 20 annular, in the belt 20, a plurality of recesses 20d, 20d, . . . is arranged in line along the circumferential direction on the surface (outer circumferential surface) of the outer layer 20b on the one end section 20e side of the belt 20 in the circumferential direction. Each recess 20d has a depth to the middle of the outer layer 20b. In contrast, as illustrated in FIG. 2A, on the inner circumferential surface of the other end section 20f of the belt 20, a projection 20p that can engage with the recess 20d is formed. The recess 20d on the one end section 20e side and the projection 20p on the other end section 20f side are engaged with each other, and thus it is possible to keep the belt 20 annular.

Note that, in lieu of or in addition to the engagement between the recess 20d and the projection 20p described above, for example, a hook-and-loop fastener may be configured by providing a large number of fine loops on the surface (outer circumferential surface) of the outer layer 20b on the one end section 20e side while providing a large number of fine hooks on the surface (inner circumferential surface) of the inner layer 20a on the other end section 20f side. By providing this hook-and-loop fastener, the one end section 20e and the other end section 20f of the belt 20 can be reliably fixed to each other.

In addition, in order to keep the belt 20 annular at all times, a curler having appropriate flexibility may be interposed in the belt 20, for example, between the fluid bag 21 and the outer layer 20b along the circumferential direction.

The main body 10 is integrally attached to and disposed at a section of the belt 20 which is a substantially central section between the one end section 20e and the other end section 20f in the circumferential direction. In this example, the section where the main body 10 is disposed is intended to correspond to the volar surface (surface corresponding to the palm side) 90a of the left wrist 90 in the worn state (see FIG. 5 to be described later).

The main body 10 has a three-dimensional shape having a thickness in a direction perpendicular to the outer circumferential surface of the belt 20. The main body 10 is formed to be small and thin so as not to become a hindrance in user's daily activities. In this example, as FIG. 2A clearly illustrates, the main body 10 has a trapezoidal contour projecting outward from the belt 20. More specifically, side surfaces 10e, 10f corresponding to both sides in the circumferential direction of the main body 10 are formed to be symmetric with respect to a center line C of the main body 10. The side surfaces 10e, 10f are inclined so as to be closer to the center line C than to the normal line N to the outer circumferential surface of the belt 20 as the surfaces 10e, 10f go farther from the belt 20. An inclination angle δ of the side surface 10f with respect to the normal line N is preferably in the range of, for example, 30° to 70°, and more preferably in the range of 40° to 60°. In this example, δ≈50°. As FIG. 2D clearly illustrates, side surfaces 10c, 10d of the main body 10 corresponding to both sides in the width direction (direction perpendicular to the circumferential direction) are formed in parallel to each other. In addition, as FIG. 2A clearly illustrates, a surface (hereinafter referred to as a "top surface") 10a which is the outer surface of the main body 10 located on the side farthest from the left wrist 90 is curved along the circumferential direction and has a radius of curvature greater than the radius of curvature of the belt 20. The dimension in the width direction of the main body 10 substantially matches the dimension in the width direction of the belt 20.

On the top surface 10a of the main body 10, an operation unit 52 for receiving an instruction from the user is provided. On the side surface 10f of the main body 10, a display device 50 serving as a display screen is provided. This side surface 10f corresponds to the side surface section of the main body 10, which is the outer surface of the main body 10 on the side facing the radial surface (section corresponding to the thumb side of the outer circumferential surface of the left wrist 90) 90c of the left wrist 90 in the worn state (see FIG. 5 to be described later). A micro USB (Universal Serial Bus) connector 58 is provided on the side surface 10e of the main body 10.

An alignment mark 29 extending in the width direction is formed on the outer circumferential surface of the belt 20 along the side surface 10f of the main body 10. The alignment mark 29 is used for positioning the instrument 1 around the left wrist 90 when the instrument 1 is worn around the left wrist 90.

The battery housing case 10A is disposed at a section of the belt 20 separated from the main body 10 in the circumferential direction. In this example, the battery housing case 10A is integrally attached to and disposed at the other end section 20f of the belt 20 on the outer side. The battery housing case 10A houses the battery 53 (see FIG. 3), and in this example, has a three-dimensional shape, more specifically, a flat substantially rectangular parallelepiped shape. As described above, the battery housing case 10A is disposed at the other end section 20f of the belt 20 on the outer side. Therefore, existence of the battery housing case 10A (and, accordingly, the battery 53) does not become an obstacle when the left wrist 90 is pressed with the belt 20.

Figure 3:
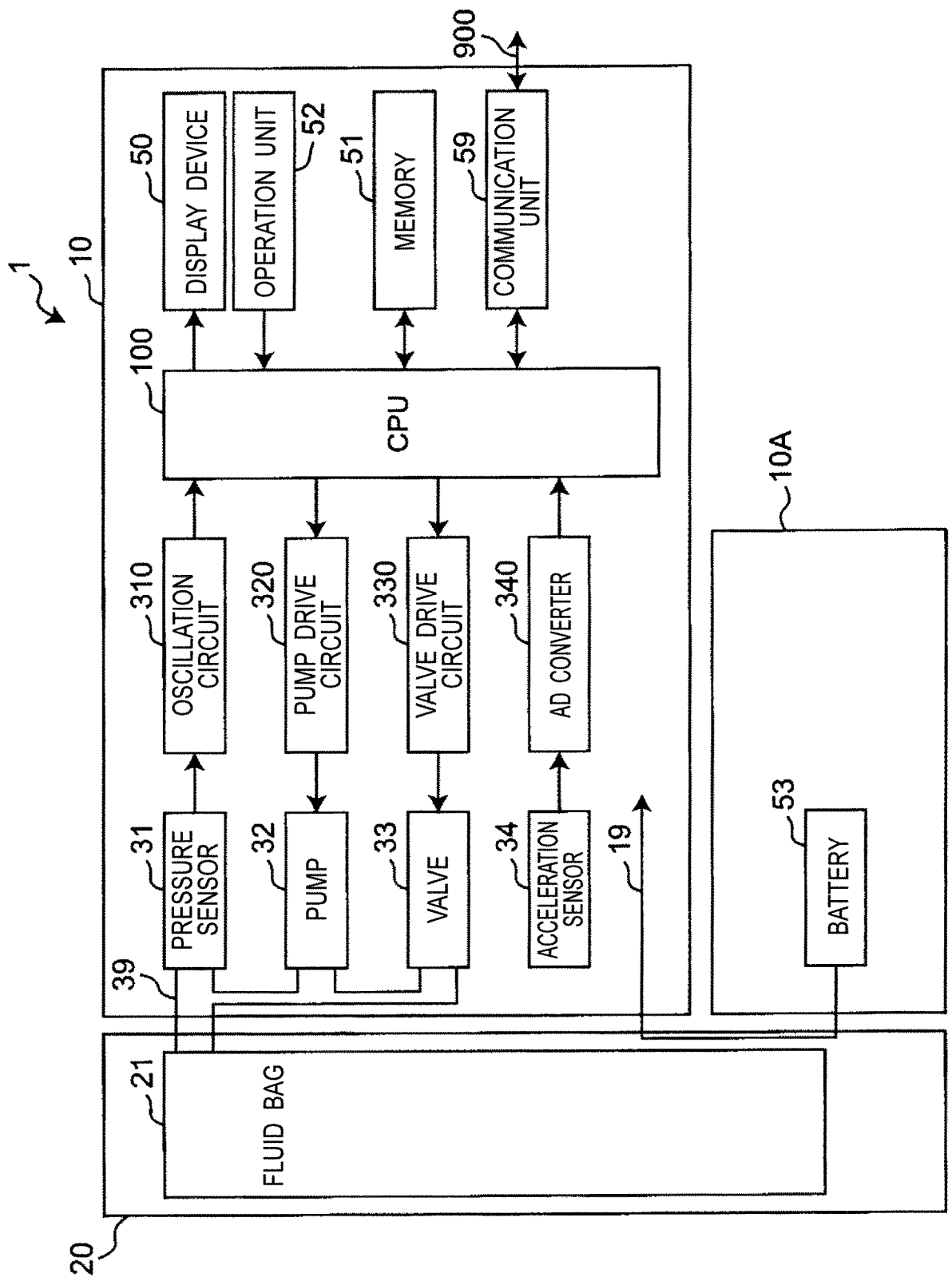
FIG. 3 is a diagram illustrating a block configuration of the instrument.

FIG. 3 illustrates a block configuration of the instrument 1. The instrument 1 has a plurality of functions such as a clock function, a body-temperature measuring function, an activity-amount measuring function, and the like in addition to the blood pressure measuring function.

In the main body 10 of the instrument 1, in addition to the above-described display device 50 and the operation unit 52, a CPU (Central Processing Unit) 100 serving as a control unit, a memory 51 serving as a storage unit, a communication unit 59, a pump 32, a valve 33, a pressure sensor 31, and an acceleration sensor 34 are mounted as elements for executing the plurality of functions. Furthermore, in the main body 10, an oscillation circuit 310 for converting output from the pressure sensor 31 to frequency, a pump drive circuit 320 for driving the pump 32, a valve drive circuit 330 for driving the valve 33, and an AD converter 340 for performing AD (Analog to Digital) conversion on output from the acceleration sensor 34 are mounted.

In this example, the display device 50 is an organic EL (Electro Luminescence) display, and displays information related to blood pressure measurement such as a blood pressure measurement result and other information, according to a control signal from the CPU 100. Note that the display device 50 is not limited to the organic EL display and may be configured of another type of display device such as an LCD (Liquid Crystal Display).

In this example, the operation unit 52 is configured of a push-type switch and transmits to the CPU 100 an operation signal corresponding to an instruction to start or stop blood pressure measurement given by the user. Note that the operation unit 52 is not limited to the push-type switch. For example, the operation unit 52 may be a pressure-sensitive-type (resistance-type) or a proximity-type (capacitance-type) touch-panel-type switch. In addition, the operation unit 52 may include a microphone, not illustrated, and may be configured to receive a voice instruction to start blood pressure measurement from the user.

The memory 51 stores in a non-transitory manner, data of a program for controlling the instrument 1, data used for controlling the instrument 1, setting data for setting various functions of the instrument 1, data of a measurement result of a blood pressure value, and the like. In addition, the memory 51 is used as a working memory or the like when the program is executed.

The CPU 100 executes various functions as the control unit according to the program for controlling the instrument 1 stored in the memory 51. For example, in a case of executing the blood pressure measuring function, the CPU 100 performs control to drive the pump 32 and the valve 33 according to an operation signal from the operation unit 52. In addition, the CPU 100 performs control to calculate a blood pressure value according to a signal from the pressure sensor 31. Furthermore, according to output from the acceleration sensor 34, the CPU 100 performs control to measure the posture of the left wrist 90, the activity amount, and the like of the user.

The communication unit 59 is controlled by the CPU 100 to transmit predetermined information to an external device via a network 900, receives information from an external device via the network 900, and forwards the information to the CPU 100. Communication via the network 900 may be either wireless or wired. In this embodiment, the network 900 is the Internet. However, the network 900 is not limited to this, and may be another type of network such as an in-hospital LAN (Local Area Network) or one-to-one communication using a USB cable or the like. The communication unit 59 includes the above-described micro USB connector 58.

The pump 32, the valve 33, and the pressure sensor 31 are connected to the fluid bag 21 contained in the belt 20 via a common air pipe 39 serving as a pipe system. The pump 32 supplies air to the fluid bag 21 through the air pipe 39 in order to increase the pressure (cuff pressure) in the fluid bag 21 contained in the belt 20. The valve 33 is a solenoid valve in which opening and closing thereof is controlled by energization, and is used to discharge the air in the fluid bag 21 through the air pipe 39 or encloses the air in the fluid bag 21 in order to control the cuff pressure. The pump drive circuit 320 drives the pump 32 according to a control signal transmitted from the CPU 100. The valve drive circuit 330 opens and closes the valve 33 according to a control signal transmitted from the CPU 100.

The pressure sensor 31, in this example, is a piezoresistive pressure sensor, and measures pressure in the belt 20 (fluid bag 21), in this example, pressure in the case of setting atmospheric pressure as the reference (zero), through the air pipe 39 and outputs the pressure as a time-series cuff pressure signal Pc. The oscillation circuit 310 oscillates according to an electric signal value based on a change in electric resistance due to the piezoresistive effect from the pressure sensor 31, and outputs a frequency signal having a frequency corresponding to the electric signal value of the pressure sensor 31 to the CPU 100.

In this example, output of the pressure sensor 31 is used to calculate blood pressure values (including systolic blood pressure and diastolic blood pressure) by an oscillometric method. In addition, output of the pressure sensor 31 is used to calculate a pulse.

As can be understood, the pressure sensor 31, the pump 32, the valve 33, the oscillation circuit 310, the pump drive circuit 320, the valve drive circuit 330, and the CPU 100 configure a pressure control unit for supplying air to the fluid bag 21 and controlling pressure in the fluid bag 21.

The acceleration sensor 34 is configured of a three-axis acceleration sensor integrally incorporated in the main body 10. The acceleration sensor 34 outputs an acceleration signal to the CPU 100 via the AD converter 340. The acceleration signal represents acceleration in three directions orthogonal to one another of the main body 10, that is, of the belt 20 integrally attached to the main body 10. In this example, output from the acceleration sensor 34 is used to measure the posture of the left wrist 90, the activity amount, and the like of the user.

In the battery housing case 10A, only the battery 53 is housed. A wire 19 is provided in the belt 20. The wire 19 extends in the circumferential direction (of the belt 20) along the fluid bag 21 and electrically connects the battery 53 and the elements mounted in the main body 10. The battery 53 supplies electric power to the elements mounted in the main body 10 through the wire 19 passing through the belt 20. In this example, the elements are the CPU 100, the pressure sensor 31, the pump 32, the valve 33, the acceleration sensor 34, the display device 50, the memory 51, the communication unit 59, the oscillation circuit 310, the pump drive circuit 320, the valve drive circuit 330, and the AD converter 340.

In this instrument 1, the clock function is realized by a clock built in the CPU 100. The body-temperature measuring function is realized by using output of a thermometer, not illustrated. The activity-amount measuring function is realized by using output of the acceleration sensor 34.

Operation of Blood Pressure Measuring Function

Figure 5:
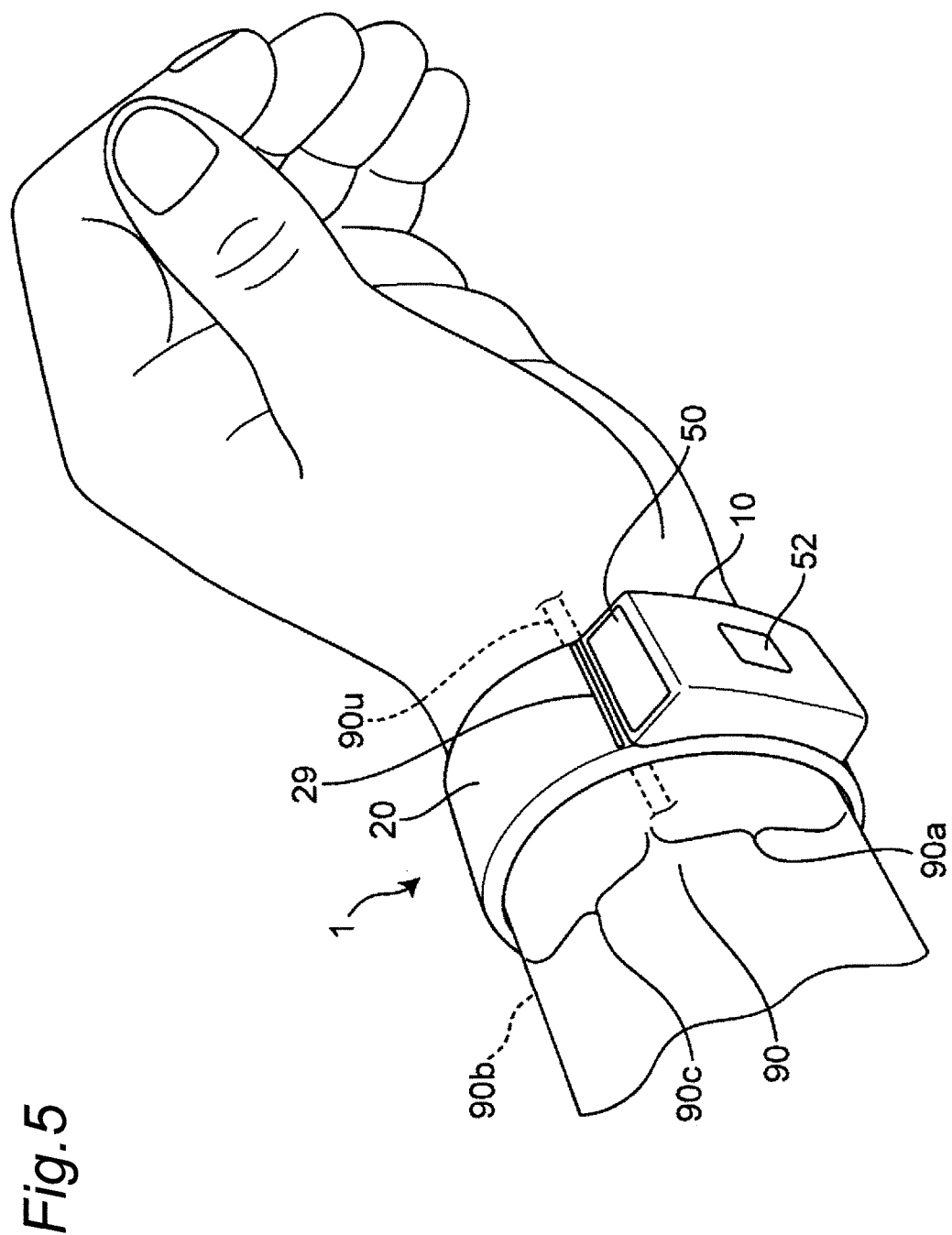
FIG. 5 is a view illustrating a state where the instrument is worn around the left wrist of a user.

When the instrument 1 is worn around the left wrist 90, the user puts the left hand through the belt 20, in a state where engagement between the one end section 20e and the other end section 20f of the belt 20 is released, in the direction indicated by arrow A in FIG. 1. Then, as illustrated in FIG. 5, the user adjusts the angular position of the belt 20 around the left wrist 90 to position the alignment mark 29 of the belt 20 on an artery 90u passing through the left wrist 90. In this state, the user selects an appropriate recess 20d, from among the recesses 20d, 20d, . . . on the one end section 20e side of the belt 20, according to the perimeter of the left wrist 90 of the user (the recess 20d at which the length of the ring of the belt 20 matches the perimeter of the left wrist 90). Then, the user engages the recess 20d with the projection 20p on the other end section 20f side. In this manner, the instrument 1 is worn around the left wrist 90. In the above worn state, the main body 10 is disposed correspondingly to the volar surface 90a of the left wrist 90, and the battery housing case 10A is disposed correspondingly to the dorsal surface 90b of the left wrist 90. The display device 50 is oriented to the radial surface 90c of the left wrist 90.

Figure 6B:
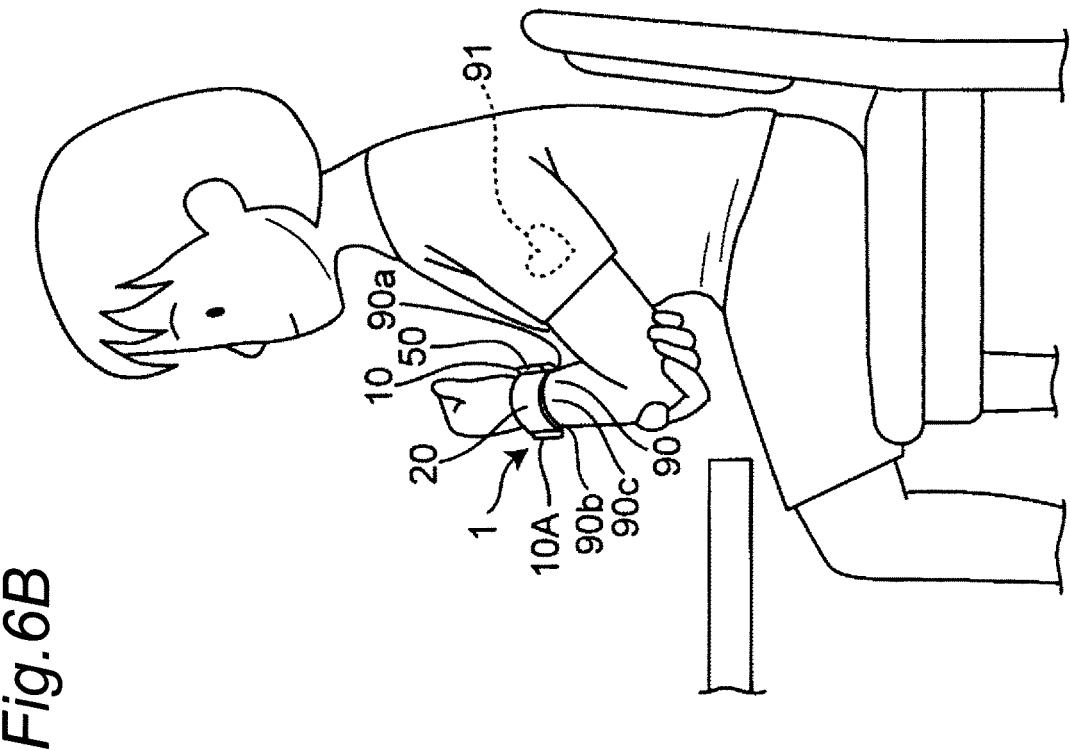
FIGS. 6A and 6B illustrate a state where a user wears the instrument around the left wrist and takes a recommended blood pressure measurement posture, as viewed from the front of the user, and from the left side of the user, respectively.
Figure 6A:
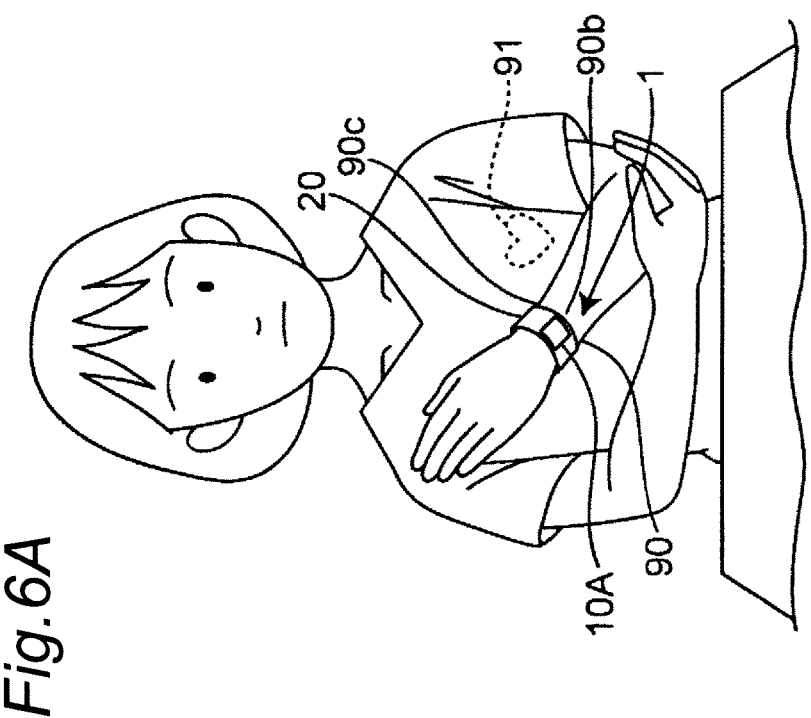

In this worn state, in order to measure blood pressure, for example, in accordance with the instruction manual of the product, the user takes a recommended blood pressure measurement posture as illustrated in FIGS. 6A and 6B. In the posture, the front arm is crossed with the trunk (with the hand up and the elbow down) in front of the trunk, the left wrist 90 is held at the height of the heart 91 and the radial surface 90c of the left wrist 90 is turned upward. Then, the display device 50 is directed upward. In addition, as illustrated in FIG. 2A, the side surface 10f, which is the outer surface of the main body 10 on which the display device 50 is disposed, is inclined so as to be closer to the center line C than to the normal line N to the outer circumferential surface of the belt 20 as the side surface 10f goes farther from the belt 20. Therefore, when the user takes the recommended blood pressure measurement posture (FIGS. 6A and 6B), the display device (display screen) 50 becomes close to perpendicular to the user's line of sight in the circumferential direction of the left wrist 90.

In this state, when the user pushes the push-type switch serving as the operation unit 52 provided on the main body 10 with the right hand, blood pressure measurement is started.

Figure 4:
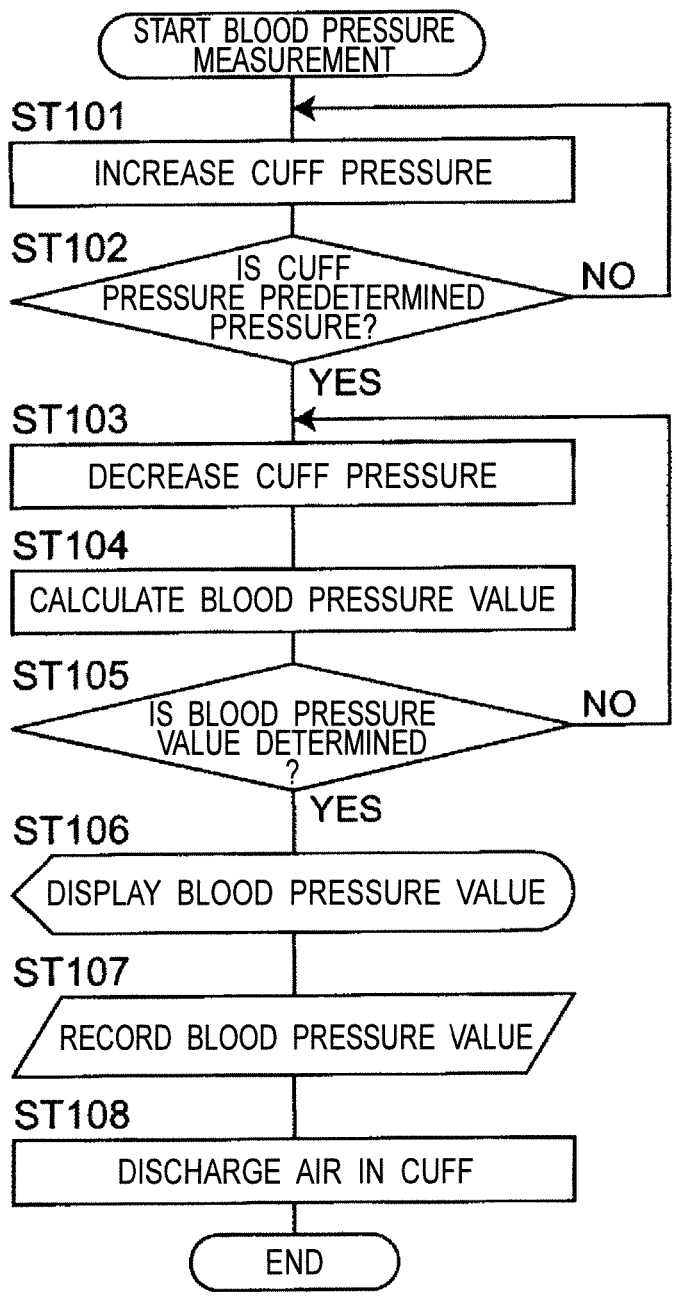
FIG. 4 is a diagram illustrating an operation flow when the instrument performs blood pressure measurement.

FIG. 4 illustrates an operation flow when the instrument 1 performs blood pressure measurement. Upon start of blood pressure measurement, the CPU 100 initializes a memory area for processing and outputs a control signal to the valve drive circuit 330. The valve drive circuit 330 opens the valve 33 according to the control signal and discharges the air in the fluid bag 21 of the belt 20. Subsequently, control for performing 0 mmHg adjustment of the pressure sensor 31 is executed.

During a blood pressure measurement period (including a preparation period), the CPU 100 causes the display device 50 to display the progress status of blood pressure measurement, in this example, in the form of a progress bar. The progress bar is a horizontal bar extending from 0% to 100% according to the progress.

When the blood pressure measurement is started, first, the CPU 100 causes the valve drive circuit 330 to close the valve 33, and then causes the pump drive circuit 320 to drive the pump 32 to supply air to the fluid bag 21. Thus, the fluid bag 21 is inflated and the cuff pressure is gradually increased (step ST101 in FIG. 4). As a result, the artery 90u of the left wrist 90 is compressed.

When the cuff pressure is applied and reaches a predetermined pressure (YES in step ST102), the CPU 100 stops the pump 32 via the pump drive circuit 320, and then causes the valve drive circuit 330 to gradually open the valve 33. Thus, the fluid bag 21 is contracted and the cuff pressure is gradually decreased (step ST103).

Here, the predetermined pressure is a pressure which is sufficiently higher than the systolic blood pressure of a subject (for example, systolic blood pressure+30 mmHg). The predetermined pressure is stored, in advance, in the memory 51 or is estimated and determined by the CPU 100 according to a predetermined calculation formula while the cuff pressure is increased (see, for example, JP 2001-70263 A).

Regarding a pressure decrease rate, a target pressure decrease rate which is a target is set while the cuff pressure is increased, and the CPU 100 controls the opening degree of the valve 33 such that the target pressure decrease rate is realized (see JP 2001-70263 A).

In the pressure decreasing process described above, the pressure sensor 31 measures the pressure of the belt 20 and outputs a cuff pressure signal Pc. According to the cuff pressure signal Pc, the CPU 100 calculates blood pressure values (systolic blood pressure and diastolic blood pressure) by using the oscillometric method and applying a known algorithm (step ST104). In addition, the CPU 100 also calculates a pulse according to the cuff pressure signal Pc. Note that the blood pressure values and the pulse may not be calculated during the pressure decreasing process, but may be calculated during the pressure increasing process.

If the CPU 100 calculates and determines the blood pressure value (YES in step ST105), the CPU 100 displays, on the display device 50, the blood pressure values obtained by the blood pressure measurement as information on the blood pressure measurement (step ST106). In addition, the CPU 100 performs control to store the blood pressure values in the memory 51 (step ST107).

The blood pressure values are displayed, for example, in the following manner. A message such as "highest blood pressure: 120 mmHg, lowest blood pressure: 80 mmHg" is displayed on the display device 50. In addition, the pulse may be displayed, for example, by displaying a message such as "pulse: 70 beats/minute".

Upon completion of the measurement, the CPU 100 causes the valve drive circuit 330 to open the valve 33 and performs control to discharge the air in the fluid bag 21 of the belt 20 (step ST108). Thus, blood pressure measurement is terminated.

As described above, the CPU 100 displays on the display device 50, the progress status of the blood pressure measurement and the blood pressure values obtained by the blood pressure measurement, as information on the blood pressure measurement.

Here, if the user takes the recommended blood pressure measurement posture (FIGS. 6A and 6B) during the blood pressure measurement period, the side surface 10f, which is the outer surface of the main body 10 on which the display device 50 is disposed, is directed upward. Therefore, the user sees the display device (display screen) 50 directed upward from above. In addition, in this example, the side surface 10f on which the display device 50 is disposed is inclined in a direction away from the radial surface 90c of the left wrist 90 with respect to the normal line N to the outer circumferential surface of the belt 20. As a result, the display device 50 becomes close to perpendicular to the user's line of sight in the circumferential direction of the left wrist 90. Therefore, display content becomes easier to see for the user than that in a conventional example. As a result, it is possible to prevent the user from consciously or unconsciously twisting the left wrist 90 and turning the dorsal surface (surface corresponding to the back-of-hand side) 90*b* of the left wrist 90 upward. Therefore, blood pressure measurement accuracy can be improved.

In this instrument 1, the battery 53 for supplying electric power to the elements mounted in the main body 10 is disposed at a portion of the belt 20 located away from the main body 10 in the circumferential direction around the left wrist 90. Therefore, it is possible to avoid the configuration in which the battery 53 is housed in the main body 10. As a result, the outer dimensions of the main body 10 such as the thickness in the direction perpendicular to the outer circumferential surface of the left wrist 90 can be reduced. In addition, the elements for executing the functions, other than the battery 53, are mounted not in a location away from the main body 10 but in the main body 10. Therefore, it is possible to prevent the configuration of the entire instrument 1 from becoming complicated.

Figure 7:
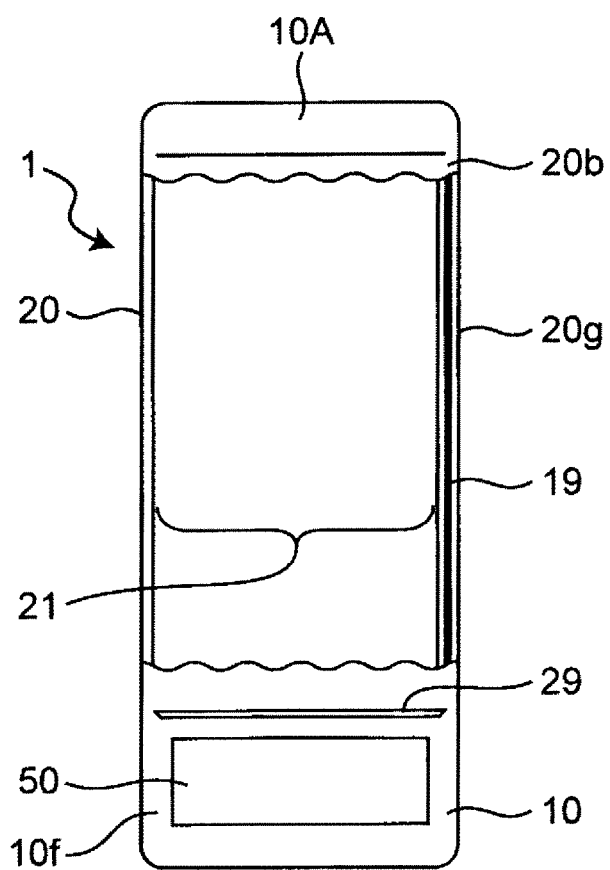
FIG. 7 is a view illustrating arrangement of a fluid bag and a wire in a belt, with omission of a part of an outer layer of the belt in FIG. 2C.

FIG. 7 illustrates arrangement of the fluid bag 21 and the wire 19 in the belt 20, with omission of a part of the outer layer 20*b* of the belt 20 in FIG. 2C. As can be seen from FIG. 7, in this example, the wire 19 is disposed, in the belt 20, along an edge section 20*g* away from the fluid bag 21 in the width direction. The reason for this is as follows. That is, if the wire 19 were disposed so as to overlap the fluid bag 21 in the width direction in the belt 20, due to expansion or contraction of the fluid bag 21 during blood pressure measurement, the fluid bag 21 and the wire 19 would be shifted relative to each other while being rubbed with each other. As a result, there would be a possibility that noise would be generated in a cuff pressure signal Pc (and, accordingly, a pulse wave signal obtained as a variation component of the cuff pressure signal Pc) during blood pressure measurement. In addition, there would be a possibility that the wire 19 would be repeatedly bent and broken. Therefore, in this instrument 1, as described above, the wire 19 is disposed, in the belt 20, away from the fluid bag 21 in the width direction and disposed along the edge section 20*g*. Thereby, it is possible to prevent noise from occurring in the cuff pressure signal Pc (and, accordingly, the pulse wave signal obtained as a variation component of the cuff pressure signal Pc) during blood pressure measurement. In addition, it is possible to prevent the wire 19 from being broken.

Figure 8A:
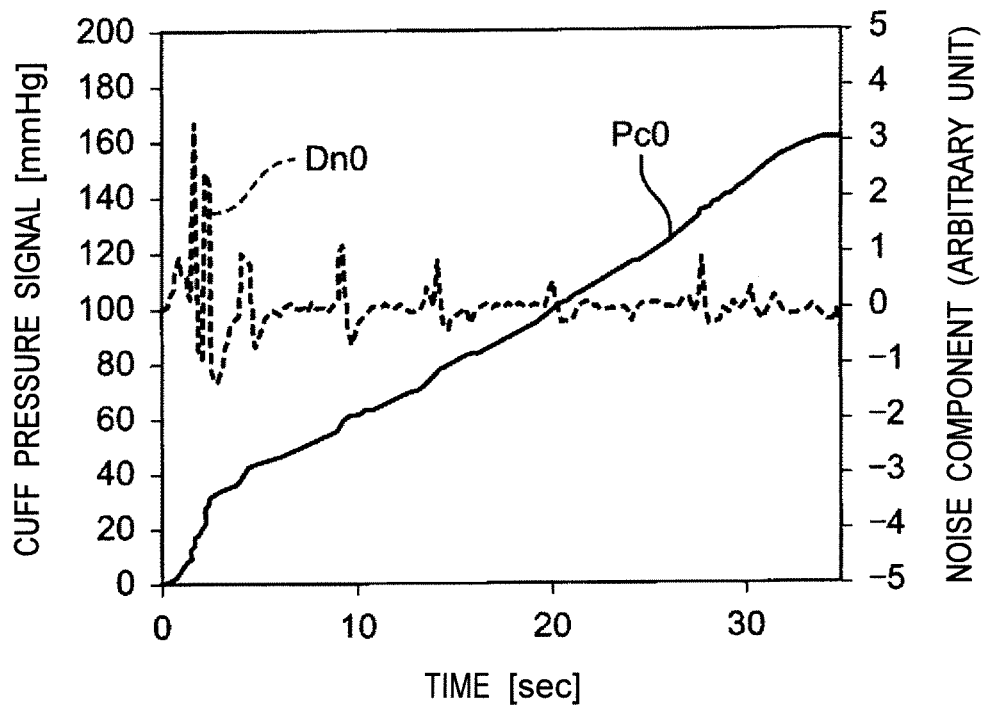
FIG. 8A is a diagram illustrating a cuff pressure signal and a noise component during blood pressure measurement in an arrangement in which the wire overlaps the fluid bag in the width direction in the belt.
Figure 8B:
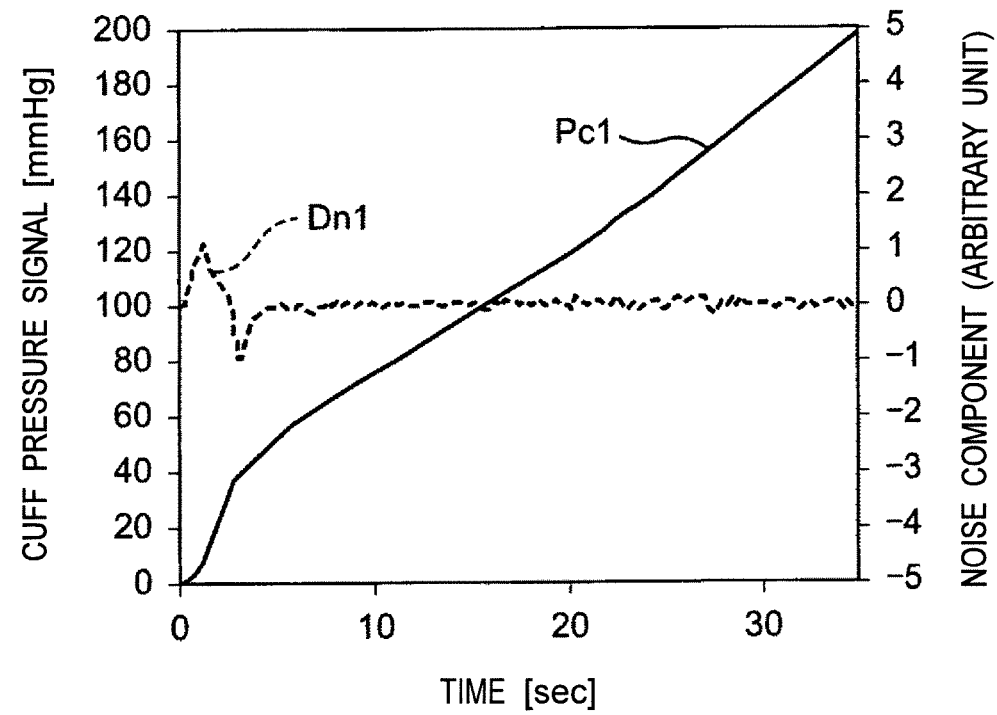
FIG. 8B is a diagram illustrating a cuff pressure signal and a noise component during blood pressure measurement in an arrangement in the belt in which the wire is located away from the fluid bag in the width direction and located along an edge section of the belt.

FIGS. 8A and 8B illustrate verification results of noise with respect to the cuff pressure signal Pc, obtained by the present inventors. FIG. 8A illustrates a cuff pressure signal Pc0 (indicated by a solid line) and a noise component Dn0 (indicated by a broken line) obtained as a variation component of the cuff pressure signal Pc0 during blood pressure measurement in an arrangement in which the wire 19 overlaps the fluid bag 21 in the width direction in the belt 20. FIG. 8B illustrates a cuff pressure signal Pc1 (indicated by a solid line) and a noise component Dn1 (indicated by a broken line) obtained as a variation component of the cuff pressure signal Pc1 during blood pressure measurement in the arrangement in the belt 20 in which the wire 19 is disposed away from the fluid bag 21 in the width direction and disposed along the edge section 20*g* as illustrated in FIG. 7. In the cuff pressure signal Pc0 in FIG. 8A, pulsed noise sometimes occurs, which is interpreted as a frictional shift between the fluid bag 21 and the wire 19. In contrast, in the cuff pressure signal Pc1 in FIG. 8B, such pulsed noise is eliminated except for initial noise (in a period of several seconds following the start of increasing the pressure).

In the above embodiment, the battery housing case 10A is disposed on a section of the belt 20 corresponding to the dorsal surface 90*b* of the left wrist 90. However, the present invention is not limited to this. The battery housing case 10A (and, accordingly, the battery 53) may be disposed at a portion of the belt 20 located away from the main body 10 in the circumferential direction around the left wrist 90. For example, the battery housing case 10A may be disposed on a portion of the belt 20 corresponding to the radial surface 90*c* of the left wrist 90 or a portion of the belt 20 corresponding to an ulnar surface (portion corresponding to the little finger side of the outer circumferential surface of the wrist).

In the above embodiment, the main body 10 is intended to be disposed correspondingly to the volar surface 90*a* of the left wrist 90. However, the present invention is not limited to this. In another specification, the main body 10 may be disposed correspondingly to the dorsal surface 90*b* of the left wrist 90. In the specification, for example, the alignment mark 29 in FIG. 1 and FIG. 7 is provided on a portion of the outer circumferential surface of the belt 20 that is close to the battery housing case 10A (specifically, the position of the alignment mark 29 in FIG. 2A is moved from a location on the lower half of the annular belt 20 to a location on the upper half of the annular belt 20, the locations being symmetric with respect to each other), and the user puts the left hand through the belt 20 from the side opposite to the side of arrow A. Also in that case, the battery housing case 10A (and, accordingly, the battery 53) may be disposed at a portion of the belt 20 located away from the main body 10 in the circumferential direction around the left wrist 90.

In addition, in the above described embodiment, it is assumed that the instrument 1 is intended to be worn around the left wrist 90. However, the present invention is not limited to this. For example, in FIGS. 1 and 7, it is assumed that a user puts the right hand through the belt 20 from the side opposite to the side of arrow A. As a result, the instrument 1 can be conveniently used even by a left-handed user.

In addition, in the above described embodiment, the battery 53 is housed in the battery housing case 10A and attached to the belt 20. However, the present invention is not limited to this, and the battery 53 may be contained in the belt 20 without a housing case.

In the above embodiment, in order to realize the blood pressure measuring function, a configuration is adopted where the fluid bag 21 (see FIG. 3) for compressing the wrist is contained in the belt 20, and blood pressure is measured by the oscillometric method. However, the present invention is not limited to this. For example, a semiconductor sensor array including a plurality of aligned pressure sensors (piezoelectric elements) may be mounted on the inner circumferential surface of a belt 20, and blood pressure is measured by using tonometry (a method of pressing an artery passing through the wrist to a degree that part of the entire circumference of the blood vessel is flattened, and non-invasively measuring blood pressure by balancing the arterial internal pressure and the arterial external pressure with each other). That is, regarding the blood pressure measuring function, the instrument according to the present invention can take various configurations and methods in order to realize the blood pressure measuring function as long as the instrument can measure blood pressure by using the belt 20 wrapped around the wrist.

As is described above, the present disclosure provides an instrument having a blood pressure measuring function and worn around a wrist, the instrument comprising:

a band-like belt which is worn around a wrist in a circumferential direction, the band-like belt including a fluid bag that extends in the circumferential direction to compress an artery of the wrist; and a main body which is disposed at a portion of the band-like belt corresponding to one of a volar surface and a dorsal surface of the wrist, in which at least a pressure control unit that supplies air to the fluid bag and controls pressure is mounted as an element for executing the blood pressure measuring function, wherein a battery which supplies electric power to the element mounted in the main body is disposed at a portion of the band-like belt away from the main body in the circumferential direction, wherein a wire which extends in the circumferential direction along the fluid bag and electrically connects the battery and the element mounted in the main body is provided in the band-like belt, and wherein, in the band-like belt, the wire is disposed away from the fluid bag in a width direction perpendicular to the circumferential direction and is disposed along an edge section of the band-like belt.

The "volar surface" of the wrist, as used herein, means a portion of the outer circumferential surface of the wrist corresponding to the palm side. The "dorsal surface" of the wrist means a portion of the outer circumferential surface of the wrist corresponding to the back-of-hand side.

In addition, the "wrist" may be either a left wrist or a right wrist.

In the instrument according to the present disclosure, the battery for supplying electric power to the element mounted in the main body is disposed at a portion of the belt located away from the main body in the circumferential direction around the wrist. Therefore, it is possible to avoid the configuration in which the battery is housed in the main body. As a result, the outer dimensions of the main body can be reduced. For example, the thickness in the direction perpendicular to the outer circumferential surface of the wrist can be made thinner.

In addition, in this instrument, the element mounted in the main body and the battery are electrically connected by the wire extending in the circumferential direction along a fluid bag in the belt. Electric power is supplied from the battery to the element mounted in the main body through the wire, and thus blood pressure measurement can be executed.

In addition, in this instrument, the pressure control unit mounted in the main body causes air to be supplied to the fluid bag, and thus the pressure in the fluid bag is controlled. As a result, an artery of the wrist is compressed, and blood pressure measurement can be carried out, for example, by a known oscillometric method.

During this blood pressure measurement, the pressure in the fluid bag is controlled such that it expands or contracts. If the wire were disposed so as to overlap with the fluid bag in the width direction in the belt, due to expansion or contraction of the fluid bag, the fluid bag and the wire would be shifted relative to each other while being rubbed with each other. As a result, there would be a possibility that noise would be generated in a cuff pressure signal (and accordingly, a pulse wave signal) during blood pressure measurement. In addition, there would be a possibility that the wire would be repeatedly bent and broken. Therefore, in this instrument, in the belt, the wire is disposed away from the fluid bag in the width direction perpendicular to the circumferential direction and is disposed along an edge section of the belt. Thereby, it is possible to prevent noise from occurring in the cuff pressure signal (and accordingly, the pulse wave signal) during blood pressure measurement. In addition, it is possible to prevent the wire from being broken.

Note that the "element for executing the function" may include an element for executing a function other than the "blood pressure measuring function", such as a clock function, a body-temperature measuring function, an activity-amount measuring function, or the like.

In the instrument according to one embodiment, one end section and an other end section of the band-like belt overlap in the circumferential direction such that the one end section is located on an inner side and the other end section is located on an outer side in a state where the band-like belt is worn around the wrist, and wherein the battery is disposed at the other end section of the belt located on the outer side.

The "one end section" and the "other end section", as used herein, are not limited to one end and the other end, respectively, and may include a certain range.

In the instrument according to the embodiment, the one end section and the other end section of the belt overlap in the circumferential direction such that the one end section is located on the inner side and the other end section is located on the outer side, in a state where the belt is worn around the wrist. Therefore, in a case where blood pressure is measured by compressing the wrist with the belt, the wrist can be reliably compressed, and accuracy of blood pressure measurement can be improved. In addition, the battery is disposed at the other end section of the belt on the outer side. Therefore, the existence of the battery does not become an obstacle when the wrist is compressed by the belt.

In the instrument according to one embodiment, only the battery is disposed at the portion of the band-like belt where the battery is disposed.

The "only the battery is disposed", as used herein, means that no element for performing a function, other than the battery, is disposed. In other words, an element configured to solely function as a casing such as a battery housing case may be disposed. The battery may be contained in the belt or may be housed in the battery housing case and attached to the belt.

In the instrument according to the embodiment, the element for executing the function, other than the battery, is mounted not in a location away from the main body but in the main body. Therefore, it is possible to prevent the configuration of the entire instrument from becoming complicated.

As is apparent from the above, according to the instrument of the present disclosure, outer dimensions of the main body can be reduced.

It is to be noted that the various embodiments described above can be appreciated individually within each embodiment, but the embodiments can be combined together. It is also to be noted that the various features in different embodiments can be appreciated individually by its own, but the features in different embodiments can be combined.

The invention claimed is:

1. An instrument having a blood pressure measuring function and configured to be worn around a wrist, the instrument comprising:
a band-like belt configured to be worn around the wrist in a circumferential direction, the band-like belt including an edge extending in the circumferential direction and a fluid bag that extends in the circumferential direction to compress an artery of the wrist; and a main body which is disposed at a first portion of the band-like belt corresponding to at least one of a volar surface and/or a dorsal surface of the wrist, in which a pressure control unit that supplies air to the fluid bag and controls pressure is mounted as an element for executing the blood pressure measuring function, wherein:

a battery which supplies electric power to the element mounted in the main body is disposed at a second portion of the band-like belt away from the main body in the circumferential direction, a wire which enters the band-like belt directly from the main body and extends in the circumferential direction along the fluid bag is provided in the band-like belt, the wire electrically connecting the battery and the element mounted in the main body, and in a planar view viewed from a thickness direction perpendicular to an outer circumferential surface of the band-like belt, the wire is spaced apart from the fluid bag, and the wire is disposed between the fluid bag and the edge of the band-like belt.

2. The instrument according to claim 1, wherein
one end section and an other end section of the band-like belt overlap in the circumferential direction such that the one end section is located on an inner side and the other end section is located on an outer side in a state where the band-like belt is worn around the wrist, and
the battery is disposed on the other end section of the belt located on the outer side at a portion that overlaps the one end section located on the inner side.

3. The instrument according to claim 1, wherein an entirety of the battery is only disposed at the second portion of the band-like belt.

4. The instrument according to claim 1, wherein the wire does not overlap the fluid bag in the planar view.

5. The instrument according to claim 1, wherein the wire extends from the main body to the battery without overlapping with the fluid bag in the planar view.

6. The instrument according to claim 1, wherein the wire does not extend outside the main body and the band-like belt.

* * * * *